United States Patent
Kolb et al.

(10) Patent No.: US 6,713,514 B1
(45) Date of Patent: Mar. 30, 2004

(54) PPAR-γ AGONISTS AS AGENTS FOR THE TREATMENT OF TYPE II DIABETES

(75) Inventors: Hartmuth C. Kolb, East Windsor, NJ (US); Gerard McGeehan, Chester Springs, PA (US); Zhi-Cai Shi, North Brunswick, NJ (US); Laxma Reddy Kolla, North Brunswick, NJ (US); Cullen Cavallaro, Allentown, NJ (US)

(73) Assignee: Lexicon Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 09/552,477

(22) Filed: Apr. 18, 2000

Related U.S. Application Data

(60) Provisional application No. 60/175,528, filed on Jan. 11, 2000, and provisional application No. 60/130,011, filed on Apr. 19, 1999.

(51) Int. Cl.[7] ............... A61K 31/195; A61K 31/24; C07C 229/00; C07C 323/00
(52) U.S. Cl. ............... 514/563; 514/538; 562/426; 562/431; 562/445
(58) Field of Search ............... 562/431, 445, 562/426; 514/538, 563

(56) References Cited

FOREIGN PATENT DOCUMENTS

GB   WO 99/43642 A1 * 10/1999

OTHER PUBLICATIONS

Baron et al, The Pathogenesis of Adoptive Murine Autoimmune Diabetes Requires an Interaction between .alpha.4–Integrins and Vascular Cell Adhesion Molecule–1, 1994, Journal of Clinical Investigation, 93(4), pp. 1700–1708.*

* cited by examiner

*Primary Examiner*—Porfirio Nazario-Gonzalez
*Assistant Examiner*—Paul A. Zucker

(74) *Attorney, Agent, or Firm*—McDonnell Boehnen Hulbert & Berghoff

(57) ABSTRACT

N-(substituted)carbamoylaryl- and heteroaryl substituted aminopropanoic and butanoic acid compounds which are highly selective agonists for the PPAR-γ receptor or prodrugs of agonists for the PPAR-γ receptor, and are useful in the treatment of Type II diabetes (NIDDM). Specifically disclosed are compounds of the formula:

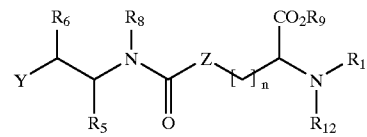

or the pharmaceutically acceptable non-toxic salts thereof wherein:

- Z is aryl or heteroaryl;
- n and m are 0, 1 or 2;
- A is a carboxylic acid or ester; or
- A is

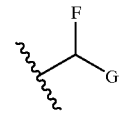

where
- D, F and G are hydrogen, (un)substituted amino, (un)substituted alkoxy, methylene or an (un)substituted sulfide;
- $R_4$ is oxo, hydrogen, hydroxy, lower alkyl, lower alkoxy, cycloalkyl, keto, acyl, or sulfonyl;
- Y is hydrogen, (un)substituted amino, (un)substituted alkoxy, methylene, an (un)substituted sulfide, (un)substituted sulfonyl or an (un)substituted sulfoxide; and
- $R_5$, $R_6$ and $R_8$ are hydrogen, lower alkyl, lower alkoxy, cycloalkyl, keto, acyl, or sulfonyl; or
- $R_5$ and $R_6$ together form a ring.

7 Claims, No Drawings

PPAR-γ AGONISTS AS AGENTS FOR THE TREATMENT OF TYPE II DIABETES

This application claims the benefit of U.S. Provisional Application No. 60/130,011, filed Apr. 19, 1999 and U.S. Provisional Application No. 60/175,528, filed Jan. 11, 2000.

BACKGROUND OF THE INVENTION

1. Field of the Invention

This invention relates to certain 1,4-disubstituted phenyl derivatives that act as agonists to the PPAR-γ receptor. This invention also relates to pharmaceutical compositions comprising such compounds. It further relates to the use of such compounds in treating Type II diabetes, or NIDDM. The interaction of certain 1,4-disubstituted phenyl derivatives of the invention with the nuclear receptor PPAR-γ is described. This interaction results in the pharmacological activities of these compounds.

2. Description of the Related Art

Type II diabetes, or non-insulin-dependent diabetes mellitus (NIDDM), is a common metabolic disorder which has no effective treatment. NIDDM occurs predominantly in adults and involves a subnormal or inadequate amount of circulating endogenous insulin. The two defects associated with NIDDM are tissue insensitivity to insulin and impaired pancreatic B-cell response to glucose. Both of these defects are further aggravated by increased hyperglycemia, and therefore many therapeutic maneuvers seek to reduce this condition.

The currently marketed oral agents for Type II diabetes fall into several classes (i) sulphonylureas (ii) biguanides, or (iii) thiazolidinedione (TZD) derivatives such as the recently approved insulin sensitizer Rezulin™, an agonist of the PPAR-γ receptor. The sulfonyureas are an older class of drug which suffer serious drawbacks such as profound hypoglycemia and cardiovascular disease. At least three mechanisms of sulfonylurea action have been proposed: (1) release of insulin from B-cells, (2) reduction of serum glucagon levels, and (3) an extrapancreatic effect to potentiate the action of insulin on its targets. Examples of sulfonyureas are tolbutamide, tolazimide, acetohexamide, chloropropamide and second generation hyperglycemic agents such as glyburide, glipizide and glimepiride.

Biguanides, such as metformin, have also been around since the mid-1950s and are generally considered as anti-hyperglycemic agents with marginal effects on insulin responsiveness. Currently proposed mechanisms of action for biguanides include (1) direct stimulation of glycolysis in tissues, with increased glucose removal from blood; (2) reduced hepatic gluconeogenesis; (3) slowing of glucose absorption from the gastrointestinal tract; and (4) reduction of plasma glucagon levels. While biguanides do not cause hyperglycemia, there is a clear need for more effective drugs that provide glycemic control and promote insulin responsiveness.

TZD derivatives are a new class of oral antidiabetic drugs in which the primary mechanism appears to be increased target tissue sensitivity to insulin. Specifically, the TZD involves binding to nuclear receptors (PPAR) that regulate the transcription of a number of insulin responsive genes critical for the control of glucose and lipid metabolism. This type of drug potentiates the action of insulin to increase glucose uptake and glucose oxidation in both muscle and adipose tissue, while reducing hepatic glucose output as well as lipid synthesis in muscle and fat cells. TZDs such as troglitazone (Rezulin™), ciglitazone, englitazone, rosiglitazone and pioglitazone are said to reduce hyperglycemia, hyperinsulinemia and hypertriglyceridemia in animal models.

The recently marketed TZD, Rezulin™, while effective, has a number of post-marketing safety problems including induction of liver enzymes (e.g. P450 3A4) and hepatotoxicity with significantly associated lethality. A newer TZD, rosiglitazone, suffers a poor pharmacokinetic profile in humans, which could limit its effectiveness in a larger population. Therefore, there is a clear need for more effective novel structures of PPAR-γ agonists that provide glycemic control and promote insulin responsiveness.

SUMMARY OF THE INVENTION

This invention provides novel compounds of Formula I that interact with the nuclear receptor PPAR-γ.

The invention provides pharmaceutical compositions comprising the compounds of Formula I. The invention also provides compounds useful in the treatment of Type II diabetes, or NIDDM. Accordingly, a broad embodiment of the invention is directed to compounds of general Formula I:

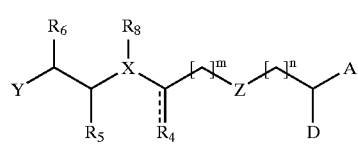

wherein:

Z is a 5 or 6 membered aryl or heteroaryl ring optionally substituted with up to three groups selected from lower alkyl, halogen or lower alkoxy;

n and m independently represent 0, 1 or 2;

A is $CO_2R_9$; or

A is

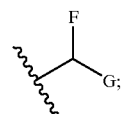

D, F and G are the same or different and represent hydrogen, $NR_1R_{12}$, $OR_1$, $CH_2R_1$ or $SR_1$;

$R_1$ and $R_{12}$ are the same or different and represent hydrogen, lower alkyl, $R_{10}C=O$, $R_{10}SO_2$, or cycloalkyl optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl, or aryl, heteroaryl, arylalkyl, or heteroarylalkyl, where the ring portion of each is optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl;

$R_{10}$ is hydrogen or lower alkyl, or aryl, heteroaryl, arylalkyl or heteroarylalkyl, where the ring portion of each is optionally substituted with one, two or three groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl;

$R_9$ is H or lower alkyl;

X is N, O, $CH_2$, S, SO or $SO_2$;

$R_4$ is O, hydrogen, hydroxy, lower alkyl, lower alkoxy, cycloalkyl, $R_{10}C=O$ or $R_{10}SO_2$;

Y is hydrogen, $NR_1R_{12}$, $OR_1$, $CH_2R_1$, $SR_1$, $SOR_1$ or $SO_2R_1$; and $R_5$, $R_6$ and $R_8$, are the same or different and represent hydrogen, lower alkyl, $R_{10}C=O$, $R_{10}SO_2$, or cycloalkyl optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl, or aryl, heteroaryl, arylalkyl, or heteroarylalkyl, where the ring portion of each is optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl; or $R_5$ and $R_6$ together with the carbon atom to which they are attached form a 5, 6, or 7 membered carbocyclic ring up to two of which members are optionally hetero atoms selected from oxygen, sulfur and nitrogen.

These compounds are highly selective agonists for the PPAR-γ receptor or prodrugs of agonists for the PPAR-γ receptor. These compounds are therefore useful in the treatment of Type II diabetes.

DETAILED DESCRIPTION OF THE INVENTION

The novel compounds encompassed by the instant invention can be described by the general Formula I set forth above or the pharmaceutically acceptable non-toxic salts thereof.

In addition, the present invention also encompasses compounds of Formula II

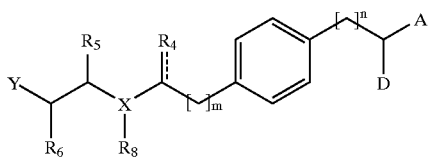

II wherein n, m, A, D, X, Y, $R_4$, $R_5$, $R_6$ and $R_8$ are as defined above for Formula I.

Preferred compounds of Formula II are where n is 1; m is 0; A is $CO_2R_9$; D is $NR_1R_{12}$; $R_4$ is O; X is N; Y is —S-aryl, —O-aryl or —$CH_2$-aryl; $R_9$ is hydrogen or lower alkyl; $R_8$ is hydrogen or lower alkyl; $R_{12}$ is hydrogen; and $R_1$ is a substituted or unsubstituted aryl or arylalkyl.

"----" refers to a bond or nothing.

By "alkyl", "lower alkyl", and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. These groups may be substituted with up to four groups mentioned below for substituted aryl.

By "alkoxy", "lower alkoxy", and "$C_1$–$C_6$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. These groups may be substituted with up to four groups mentioned below for substituted aryl.

By the term "halogen" in the present invention is meant fluorine, bromine, chlorine, and iodine.

A "carbocyclic group" or "cycloalkyl" is a nonaromatic cyclic ring or fused rings having from 3 to 7 ring members. Examples include cyclopropyl, cyclobutyl, and cycloheptyl. These rings may be substituted with one or more of the substituent groups mentioned below for aryl, for example alkyl, halo, amino, hydroxy, and alkoxy. Typical substituted carbocyclic groups include 2-chlorocyclopropyl, 2,3-diethoxycyclopentyl, and 2,2,4,4-tetrafluorocyclohexyl. The carbocyclic group may contain one or two heteroatoms selected from oxygen, sulfur, and nitrogen, and such ring systems may be referred to as "heterocyclyl" or "heterocyclic". Examples include pyranyl, tetrahydrofuranyl, and dioxanyl. These heterocyclyl groups may be substituted with up to four of the substituent groups mentioned for aryl to give groups such as 3-chloro-2-dioxanyl, and 3,5-dihydroxymorpholino.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. The heteroaryl group is optionally substituted with up to four groups mentioned below for substituted aryl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, —OH, —SH, lower alkyl, lower alkoxy, lower alkylthio, trifluoromethyl, trifluoromethoxy, lower acyloxy, aryl, heteroaryl, amino, mono- or kialkylamino, and nitro, . A preferred aryl is phenyl.

In certain situations, compounds of Formula I and Formula II may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the invention are shown below in Table 1.

TABLE 1
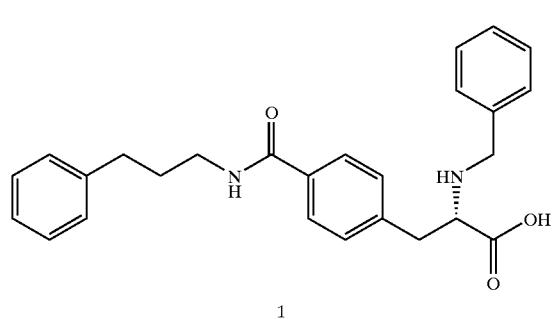
1
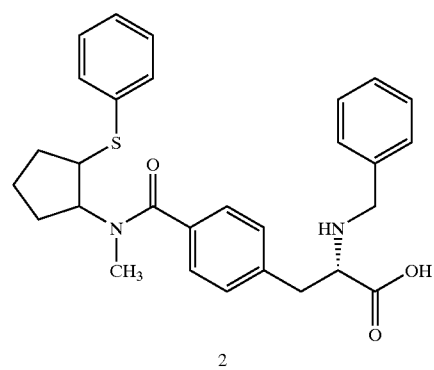
2
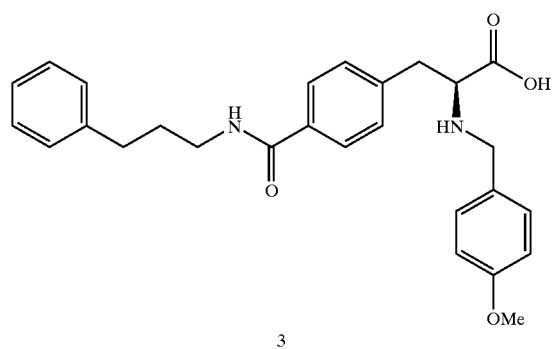
3
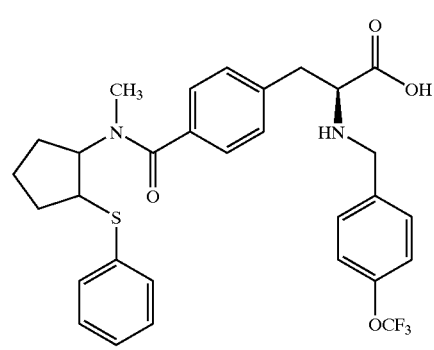
4
TABLE 1-continued
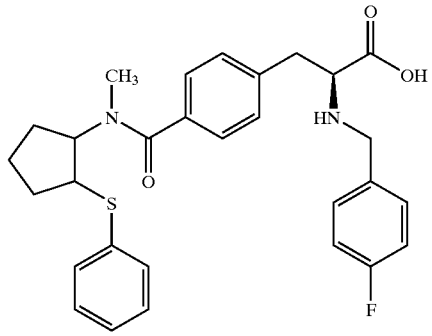
5
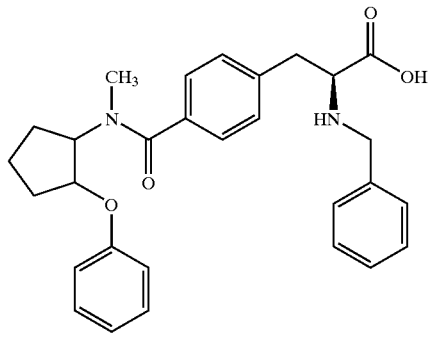
6
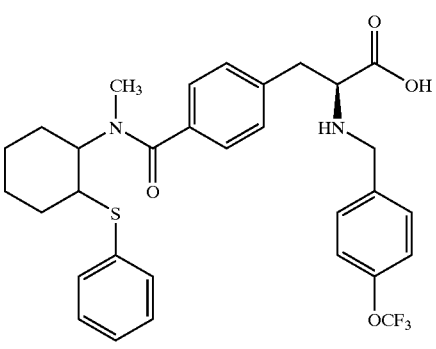
7
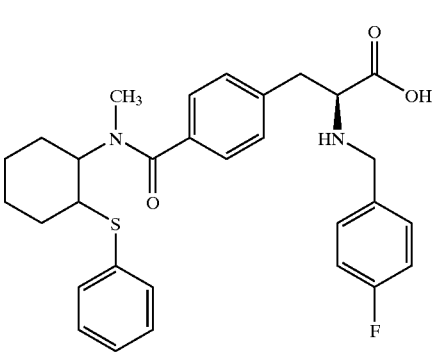
8

Representative compounds of the present invention, which are encompassed by Formula I, include, but are not limited to the compounds in Table I and their pharmaceutically acceptable salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydriodic, alkanoic such as acetic, $HOO-(CH_2)_n-CO_2H$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The compounds of Formula I and their salts are suitable for the treatment of Type II diabetes, both in human and non-human animals and domestic pets or companion animals, especially dogs and cats and farm animals such as sheep, swine and cattle.

The compounds of general Formula I may be administered orally, topically, parenterally, by inhalation or spray, or rectally in unit dosage formulations containing conventional non-toxic pharmaceutically acceptable carriers, adjuvants, and vehicles. The term parenteral as used herein includes subcutaneous injections, intravenous, intramuscular, intrasternal injection or infusion techniques. In addition there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared by any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, cornstarch or align acid; binding agents, for example starch, gelatin, or acacia; and lubricating agents, for example, magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distaerate may be employed.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials with excipients suitable for the manufacture of aqueous suspensions. Such excipients are suspending agents, for example, sodium cerboxymethylcellulose, methylcellulose, hydropropylmethyl-cellulose, sodium alginate, polyvinylpyrrolidone, gum tragacanth, and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols. for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitanmonooleate. The aqueous suspensions may also contain one or more preservatives, for example, ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example sweetening, flavoring, and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan momoleate. The emulsions may also contain sweetening and flavoring agents.

Syrups and elixirs may be formulated with sweetening agents, for example glycerol, propylene glycol, sorbitol, or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or digylcerides. In addition, fatty acids such as oleic acid find use in the preparation of injecatables.

The compounds of general Formula I may also be administered in the form of suppositories for rectal administration of the drug. These compositions can be prepared by mixing the drug with a suitable non-irritating excipient which is solid at ordinary temperatures but liquid at rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

It will be understood that the specific dose level for any particular patient will depend upon a variety of factors including the activity of the specific compound employed, the patient's age, body weight, general health, sex, and diet, and the time of administration, route of administration, rate of excretion, drug combination, and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Scheme I and Scheme II. In Scheme II, the groups $R_5$, $R_6$, $R_8$ and Y are as defined in general Formula I; and $R_3$ is hydrogen, lower alkyl, or
aryl, heteroaryl, arylalkyl, or heteroarylalkyl, where the ring portion of each is optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl, or $R_3$ together with the carbon atom to which it is attached forms an optionally substituted cycloalkyl.

SCHEME I
Scaffold Synthesis

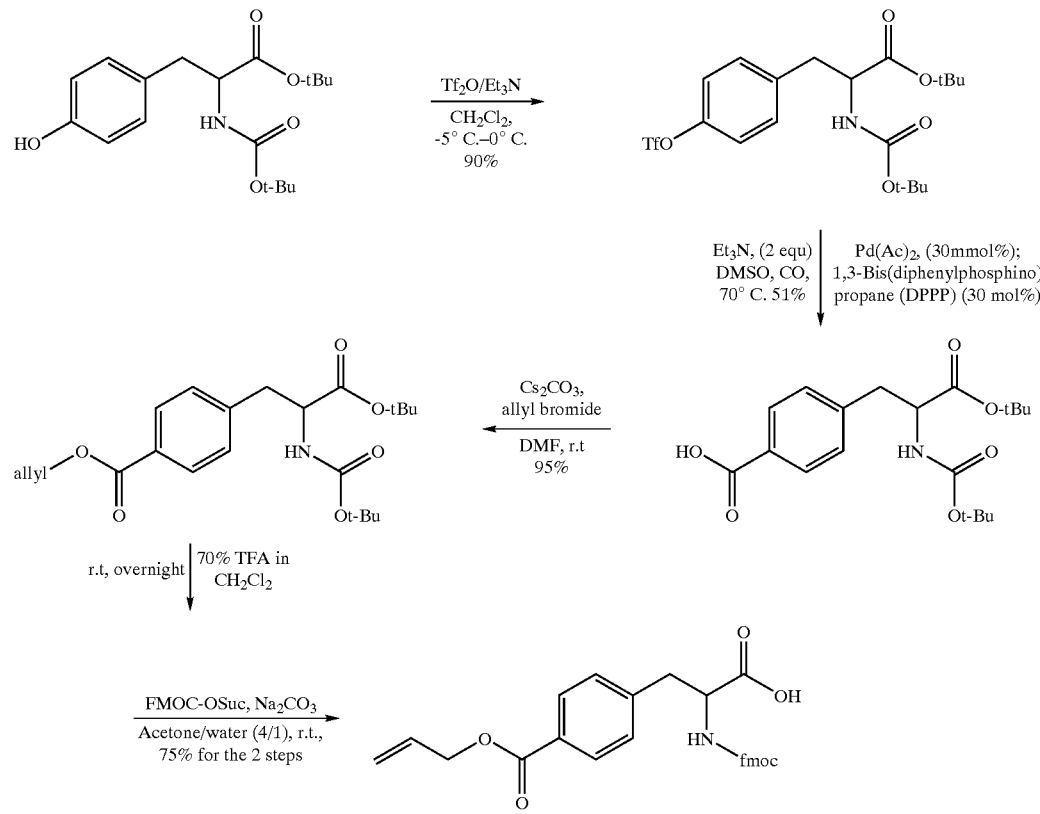

SCHEME II
Library Synthesis

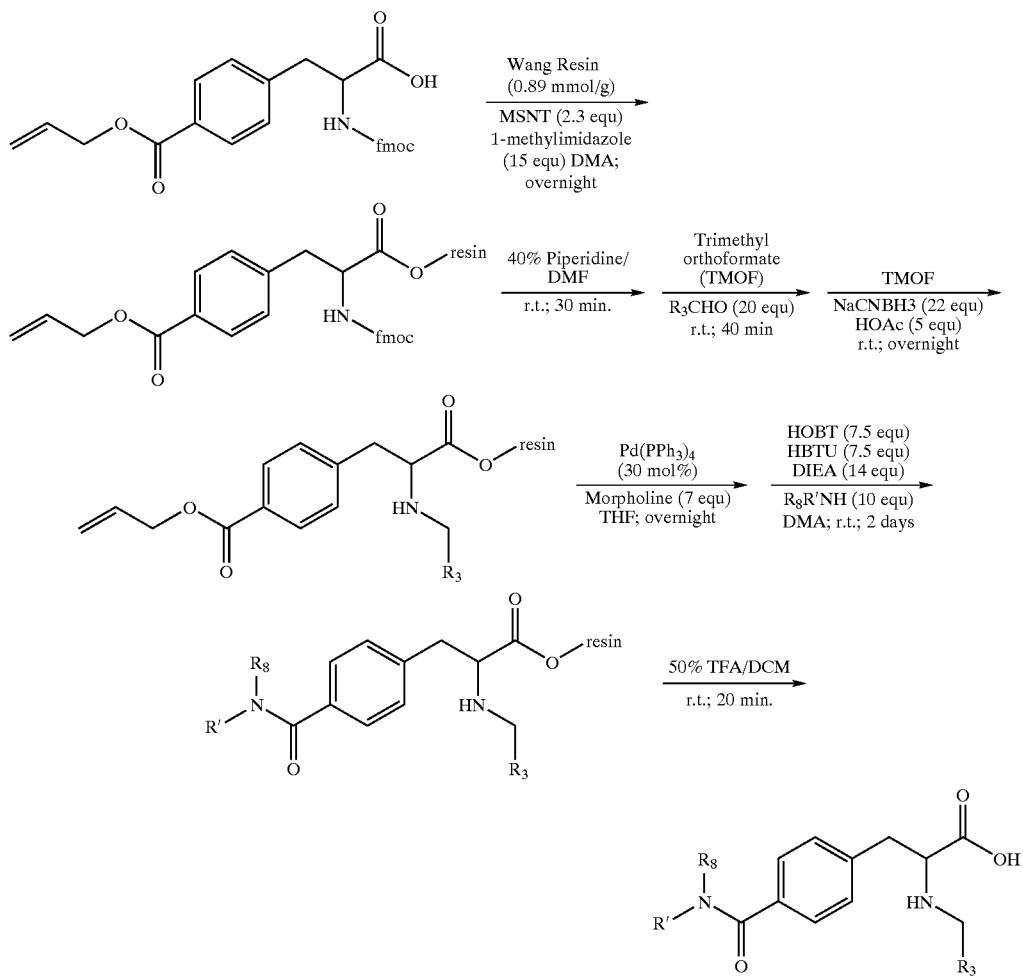

MSNT = 1-(Mesitylene-2-sulfonyl)-3-nitro-1,2,4-triazole

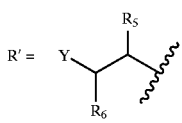

Those having skill in the art will recognize that the starting materials may be varied and additional steps employed to produce compounds encompassed by the present invention, as demonstrated by the following examples.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

1. Loading scaffold on Wang Resin 6.0 g of Wang Resin (0.89 mmol/g, 5.34 mmol) is washed with DMA (N,N-dimethylacetamide) 3×40 ml, DCM (dichloromethane) 3×40 ml in the peptide vessel. The resin is then dried over a vacuum pump for 2 hrs.

The treated resin is swelled in 70 ml of DCM. 5.83 g of Fmoc-amino acid (12.38 mmol), 3.8 g of 1-(mesitylene-2-sulfonyl)-3-nitro-1,2,4-triazole (MSNT) (12.8 mmol) and 32 ml of 1-methylimidazole (402 mmol) are added subsequently. The resultant mixture is shaken on the orbital shaker (200 rpm) for 3.5 hrs. The resin is drained and washed with DMA (4×50 ml), tetrahydrofuran (THF) (4×50ml), DCM (4×50 ml) and dried under vacuum pump overnight.

2 ml of DCM and 2 ml of TFA are added to 237 mg of coupled resin in peptide vessel. The mixture is shaken at room temperature for 30 min. The resin is filtered off and washed with DCM/trifluoroacetic acid (TFA)=1/1 (3×2 ml), DCM (3×5 ml). The filtrates are combined together. Removal of solvents gives a white solid (70 mg). After the blank of resin is deducted (~6 mg), the loading efficiency of coupling reaction between Fmoc protected amino acid made and Wang resin is 0.573 mmol/g.

2. Deprotection of Fmoc Group

Dimethylformamide (DMF) (60 ml) and piperidine (40 ml) are added to Fmoc-(4-allyloxycarbonyl)-L-Tyr-Wang resin (6 g, 3.44 mmol). The mixture is shaken (200 rpm) at room temperature for 40 min. The resin is then drained and washed with DMF (3×40 ml), THF (3×40 ml), DCM (3×40 ml) and dried under high vacuum pump overnight.

3. Reductive Amination

The above amine resin is swelled in 60 ml of TMOF, and benzaldehyde (9.6 ml, 94.4 mmol) is added and the mixture is shaken for 40 min. The resin is drained and washed with TMOF (2×40 ml) to remove excess aldehyde. The resin is re-swelled in 60 ml of TMOF and sodium cyanoborohydride (5.6 g, 89.2 mmol) is added followed by 1 ml of acetic acid. The mixture is shaken (200 rpm) at room temperature overnight. The resin is then drained and washed with MeOH (3×40 ml), DMF(3×40 ml), THF (3×40 ml), DCM (3×40 ml) and dried under high vacuum pump overnight.

4. Allyl Deprotection The above resin is swelled in 60 ml of anhydrous TVF and 2.1 ml of morpholine (24.2 mmol, 7 eq.) is added followed by 1.2 g of Pd(PPh$_3$)$_4$ (30% mol). The mixture is shaken (200 rpm) at room temperature overnight. The resin is then drained and washed with HOAc (3×40 ml), DMF (3×40 ml), THF (3×40 ml), DCM (3×40 ml) and dried under a high vacuum pump 5. Coupling with 3-phenyl-1-propylaniine The above resin is swelled in 70 ml of DMA. HOBt (3.48 g, 25.8 mmol, 7.5 eq.), HBTU (9.78 g, 25.8 mmol, 7.5 eq.), DIEA (8.37 ml, 14 eq.) and 3-phenyl-1-propylamine (4.9 ml, 10 eq.) are added. The mixture is shaken (200 rpm) at room temperature for 2 days. The resin is then drained and washed with DMF (4×40 ml), THF (4×40 ml) and then DCM (4×40 ml) and dried under high vacuum pump.

6. Cleavage From Resin

The above resin is swelled in 60 ml of DCM and 40 ml of TFA is added. The mixture is shaken at room temperature for 30 min. The resin is drained and the TFA/DCM solution is collected. The resin is washed with DCM (2×30 ml) and all organic solutions are combined. Removal of solvents gives crude product, which is purified by column chromatography (SiO$_2$, CHCl$_3$/MeOH=10/1 to 4/1) to produce 811 mg of a white solid.

EXAMPLE 2

The following compounds are prepared essentially as described in example 1:

(a) (2S)-2-[benzylamino]-3-{4-[N-(3-phenylpropyl) carbamoyl]phenyl}propanoic acid (Compound 1);
(b) (2S)-3-{4-[N-methyl-N(2-phenylthiocyclopentyl) carbamoyl]phenyl}-2-[benzylamino]propanoic acid (Compound 2);
(c) (2S)-2-{[(4-methoxyphenyl)methyl]amino}-3-{4-[N-(3-phenylpropyl) carbamoyl]phenyl}propanoic acid (Compound 3);
(d) (2S)-3-{4-[N-methyl-N-(2-phenylthiocyclopentyl) carbamoyl]phenyl}-2-({[4-(trifluoromethoxy)phenyl] methyl}amino)propanoic acid (Compound 4);
(e) (2S )-2-{[(4-fluorophenyl)methyl]amino}-3-{4-[N-methyl-N-(2-phenylthiocyclopentyl)carbamoyl] phenyl}propanoic acid (Compound 5);
(f) (2S)-3-{4-[N-methyl-N-(2-phenoxycyclopentyl )carbamoyl]phenyl}-2-[benzylamino]propanoic acid (Compound 6);
(g) (2S )-3-{4-[N-methyl-N-(2-phenylthiocyclohexyl) carbamoyl]phenyl}-2-({[4-(trifluoromethoxy)phenyl] methyl}amino)propanoic acid (Compound 7); and
(h) (2S)-2-{[(4-fluorophenyl)methyl]amino}-3-{4-[N-methyl-N-(2-phenylthiocyclohexyl)carbamoyl] phenyl}propanoic acid (Compound 8).

EXAMPLE 3

Human Adipocyte Differentiatioti

Assays are carried out on primary human subcutaneous preadipocytes. Preadipocytes are inoculated at high density in preadipocyte medium (DME/F-10, 1:1, (v/v) containing 10% fetal calf serum) and maintained overnight for attachment. Drug treatment is initiated the second day by changing to serum free medium containing test compounds. The basal medium, which is used as the negative control, contains DME/F-10, biotin (33 $\mu$M), pantothenate (17 $\mu$M), insulin (100 nM), and dexamethasone (1 $\mu$M) and BRL 49653 is included as a positive control. The culture is maintained for 14 days with the compound treatment during the first five days. At the end of the culture, cells are fixed in 5% formalin and stained with oil red-O dye. The dye is extracted by isopropanol and quantitated by measure the optical density at 500 nm. EC50 values found in Table 1 reflect the human adipocyte differentiation of the compound in presence of insulin and dexamethasone.

TABLE 1

Human Adipocyte Differentiation

| Compound | EC50 Differentiation | EC50 Inhibition of Differentiation |
|---|---|---|
| 1 | 150 nm | >10 $\mu$m |
| 2 | 175 nm | >10 $\mu$m |
| Rosiglitizone | 100 nm | >10 $\mu$m |

EXAMPLE 4

Binding to PPAR-$\gamma$ Receptor Compounds are assayed for their ability to inhibit the binding of 3H-PPAR-$\gamma$ ligand to the LBD (ligand binding domain) of the PPAR-$\gamma$ receptor. Compounds are tested at 4 concentrations (1 $\mu$M to 1 nM) in triplicate. Compounds are incubated with H3-PPAR ligand (8 nM final concentration) and LBD (210 ng/assay well) in assay buffer (50 mM Tris pH8.0. 50 mM KCL, 2 mM EDTA, 0.3% CHAPS, 0.1 mg/ml BSA, 10 mM DTT) for 2 hours with gentle shaking. Non-specific binding is measured in the presence of 10 $\mu$M excess cold competitor. Bound ligand is separated using gel filtration plates (Edge Biosystems 31909) and captured on 96 well Wallac MicroBeta plates (1450–5150 by centrifugation for 5 minutes at 2500 rpm. Radioactivity is measured in a Wallac Micro Beta counter. Table 2 gives the IC50 values of compounds 1 and 2.

TABLE 2

| Compound | IC$_{50}$ ($\mu$m) |
|---|---|
| 1 | 1.7 |
| 2 | 3.3 |

EXAMPLE 5

Blood Glucose Lowering in Diabetic Rats

Male Zucker lean rats, 24–28 weeks of age, are fed high fat chow (AIN-93-M formulation) for two weeks to elevate blood glucose. At blood glucose concentrations over 160 mg/dl, a three day pre-study baseline is established by measuring blood glucose daily (at 0700–0800 hrs) via tail vein blood extraction and measurement using a glucometer. Animals are segregated into groups of 5 based on weights and baseline glucose. Compounds are then administered to the animals at various concentrations (30 mg compound/kg body weight or 10 mg compound/kg body weight). The drugs were suspended in 0.5% carboxymethylcellulose (Sigma) in a total gavage volume of 250 μL. Animals are dosed for seven days, once daily in the morning after blood glucose and weight determination. At the end of the seven-day period, the animals are euthanized by exsanguination after isofluorane anesthesia. Table 3 depicts the normalization of blood glucose in the rats.

TABLE 3

Normalization of Blood Glucose in Zucker Obese Rats

| Treatment Day | Blood Glucose (mg/dl ± SEM) | | |
|---|---|---|---|
| | Vehicle | Cmpd. 1 | Cmpd. 2 |
| 0 | 129 ± 7 | 133 ± 11 | 133 ± 11 |
| 1 | 134 ± 15 | 134 ± 11 | 136 ± 5 |
| 2 | 133 ± 7 | 105 ± 7 | 104 ± 1 |
| 3 | 129 ± 5 | 105 ± 4 | 100 ± 9 |
| 4 | 143 ± 3 | 97 ± 16 | 93 ± 6 |
| 5 | 120 ± 10 | 113 ± 3 | 100 ± 4 |
| 6 | 127 ± 5 | 105 ± 6 | 101 ± 5 |
| 7 | 132 ± 6 | 104 ± 8 | 92 ± 6 |

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regaurded as invention, the following claims conclude this specification.

What is claimed is:

1. A compound of the formula:

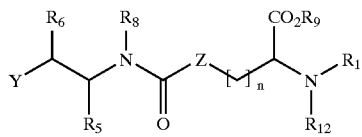

or the pharmaceutilally acceptable non-toxic salts thereof wherein:

Z is a 5 or 6 membered aryl or heteroaryl ring optionally substituted with up to three groups selected from lower alkyl, halogen or lower alkoxy;

n is 1 or 2;

$R_1$ and $R_{12}$ are the same or different and represent hydrogen, lower alkyl, $SO_2(R_{10})$, or cycloalkyl optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl, or aryl, heteroaryl, arylalkyl, or heteroarylalkyl, where the ring portion of each is optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl;

$R_{10}$ is hydrogen or lower alkyl, or aryl, heteroaryl, arylalkyl or heteroarylalkyl, where the ring portion of each is optionally substituted with one, two or three groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl;

$R_9$ is H or lower alkyl;

Y is hydrogen, $NR_1R_{12}$, $OR_1$, $CH_2R_1$, $SR_1$, $SOR_1$ or $SO_2R_1$; and $R_5$, $R_6$ and $R_8$, are the same or different and represent hydrogen, lower alkyl, $R_{10}C=O$, $R_{10}SO_2$, or cycloalkyl optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl, or aryl, heteroaryl, arylalkyl, or heteroarylalkyl, where the ring portion of each is optionally substituted with one, two, three or four groups independently selected from halogen, trifluoromethyl, trifluoromethoxy, cyano, nitro, carboxyl, alkoxycarboxy, alkylcarboxy, hydroxy, lower alkyl, lower alkoxy, amino, or mono or dialkylamino where each alkyl portion is lower alkyl; or $R_5$ and $R_6$ together with the carbon atom to which they are attached form a 5, 6, or 7 membered carbocyclic ring up to two of which members are optionally hetero atoms selected from oxygen, sulfur and nitrogen.

2. A compound of claim 1 having the formula:

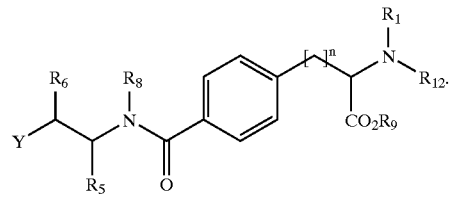

3. A compound according to claim 2 wherein n is 1.

4. A compound according to claim 2 wherein $R_8$ is selected from hydrogen or lower alkyl.

5. A compound according to claim 1 which is selected from (2S)-2-[benzylamino]-3-{4-[N-(3-phenylpropyl)carbamoyl]phenyl} propanoic acid;

(2S)-3-{4-[N-methyl-N(2-phenylthiocyclopentyl)carbamoyl]phenyl}-2-[benzylamino]propanoic acid;

(2S)-2-{[(4-methoxyphenyl)methyl]amino}-3-{4-[N-(3-phenylpropyl)carbamoyl]phenyl}propanoic acid;

(2S)-3-{4-[N-methyl-N-(2-phenylthiocyclopentyl)carbamoyl]phenyl}-2-({[4-(trifluoromethoxy)phenyl]methyl}amino)propanoic acid;

(2S)-2-{[(4-fluorophenyl)methyl]amino}-3-{4-[N-methyl-N-(2-phenylthiocyclopentyl)carbamoyl]phenyl}propanoic acid;

(2S)-3-{4-[N-methyl-N-(2-phenoxycyclopentyl)
carbamoyl]phenyl}-2-[benzylamino]propanoic acid;

(2S)-3-{4-[N-methyl-N-(2-phenylthiocyclohexyl)
carbamoyl]phenyl}-2-({[4-(trifluoromethoxy)phenyl]
methyl}amino)propanoic acid; and (2S)-2-{[(4-fluorophenyl)methyl]amino}-3-{4-[N-
methyl-N-(2-phenylthiocyclohexyl)carbamoyl]
phenyl}propanoic acid.

6. A pharmaceutical composition comprising a compound according to claim 1 and a pharmaceutically acceptable carrier.

7. A method of treating Type II diabetes in a mammal comprising administering to said mammal a compound according to claim 1

* * * * *